(12) United States Patent
Gröning et al.

(10) Patent No.: US 6,214,172 B1
(45) Date of Patent: *Apr. 10, 2001

(54) PREPARATION OF METHYLGLYOXAL DIMETHYL ACETAL

(75) Inventors: Carsten Gröning, Mannheim; Klaus Ebel; Gerd Kaibel, both of Lampertheim; Jörg Therre, Worms; Jürgen Koopmann, Neustadt; Helmuth Menig, Friedelsheim; Gerhard Fritz, Dannstadt-Schauernheim; Rainer Dietz, Neustadt, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/845,556

(22) Filed: Apr. 25, 1997

Related U.S. Application Data

(63) Continuation of application No. 08/532,851, filed on Sep. 22, 1995, now abandoned.

(30) Foreign Application Priority Data

Sep. 30, 1994 (DE) .................................................. 44 35 176

(51) Int. Cl.[7] ............................... B01D 3/36; B01D 3/38; C07C 41/58
(52) U.S. Cl. ............................... 203/14; 203/29; 203/57; 203/75; 203/76; 203/77; 203/92; 203/93; 203/98; 203/DIG. 11; 203/97; 203/94; 568/699
(58) Field of Search ............................ 203/14, 17, 91–94, 203/95–98, 29, DIG. 11, DIG. 23, 73–80, 57; 568/594, 605, 699, 414

(56) References Cited

U.S. PATENT DOCUMENTS

| | | |
|---|---|---|
| 2,421,559 | 6/1947 | Guest et al. . |
| 3,478,060 | 11/1969 | Maschke et al. . |
| 3,956,074 * | 5/1976 | Bittler .................................. 203/76 |
| 4,158,019 * | 6/1979 | Meyer ................................. 568/391 |
| 4,383,893 * | 5/1983 | Kaibel et al. ....................... 568/913 |
| 4,385,965 * | 5/1983 | Müller et al. ....................... 568/594 |
| 4,473,444 * | 9/1984 | Feldman et al. ................... 203/69 |
| 4,607,126 * | 8/1986 | Sajtos ................................. 568/385 |
| 5,137,605 * | 8/1992 | Greiner et al. ..................... 203/98 |
| 5,362,918 * | 11/1994 | Aizawa et al. ..................... 203/68 |

FOREIGN PATENT DOCUMENTS

| | | |
|---|---|---|
| 1252193 | 10/1967 | (DE) . |
| 2947383 | 6/1981 | (DE) . |
| 1473782 * | 5/1977 | (JP) . |
| 59-199651 | 4/1983 | (JP) . |

OTHER PUBLICATIONS

Braude et al, J. Chem. Soc., p. 3328 (1955).

* cited by examiner

Primary Examiner—Virginia Manoharan
(74) Attorney, Agent, or Firm—John H. Shurtleff

(57) ABSTRACT

In a process for the preparation of methylglyoxal dimethyl acetal from methylglyoxal and methanol in the presence of an acidic ion exchanger, water is introduced in an amount sufficient to form an acidic reaction mixture in which the acetal product and water form an azeotropic mixture, with or without the retention of some methanol reactant. After subjecting a single phase acidic reaction mixture to an azeotropic distillation, it will separate into two distinct liquid phases with a simple recovery of the acetal product from the aqueous phase.

5 Claims, 2 Drawing Sheets

PREPARATION OF METHYLGLYOXAL DIMETHYL ACETAL

This application is a continuation of prior application Ser. No. 08/532,851, filed Sep. 22, 1995 (abandoned).

BACKGROUND OF THE INVENTION

The present invention relates to a process for the preparation of methylglyoxal dimethyl acetal (1,1-dimethoxy-2-propanone) by reacting methylglyoxal (2-oxopropanal) with methanol in the presence of an acidic catalyst, in particular of an acidic ion exchanger.

In the previously described preparations of methylglyoxal dimethyl acetal (MGDA) from methylglyoxal (MG) and methanol, it was frequently attempted to remove the water, which can originate both from the starting methylglyoxal solution and from the reaction itself, from the mixture by means of entraining agents during the reaction (eg. Braude et al., J. Chem. Soc. 3328 (1955); Hoechst AG, DE 29 47 383). This requires the use of readily volatile, generally toxic assistants, for example benzene, which may contaminate the product. Moreover, the yields described are only 67% at the most. 1,2,2,2-Tetramethoxypropane is described as a waste product.

Furthermore, a Japanese Patent Application (JP 59199651A) describes the acetalation of methylglyoxal with methanol over ion exchangers in suspensions, working up being effected by means of extraction with methylene chloride as the solvent. Since methylglyoxal dimethyl acetal is largely used for the preparation of pharmaceutical products, the use of this toxic assistant appears unacceptable. No information is given with regard to the whereabouts of the ion exchanger and the distillation residues. In addition, our own experiments (cf. Comparative Example) show that the yields stated in JP 59199651A cannot be repeated with the methylglyoxal available in industry (about 40% strength aqueous solution). The methanol excess of 1:23 used in the Examples in this publication and the long reaction times of 16 hours are moreover disadvantageous for an industrial methylglyoxal dimethyl acetal synthesis.

It is an object of the present invention to remedy the abovementioned disadvantages in the preparation of methylglyoxal dimethyl acetal from methylglyoxal and methanol.

SUMMARY OF THE INVENTION

We have found that this object is achieved by the novel and improved process for the preparation of methylglyoxal dimethyl acetal in which, after the reaction of methylglyoxal and methanol in the presence of a catalyst, the product methylglyoxal dimethyl acetal is obtained by azeotropic distillation with water.

The process can be carried out continuously or, preferably, batchwise. For carrying out the further process, methylglyoxal, which contains more than 40% by weight of water, is preferably concentrated is to a water content of less than 40% by weight by distilling off water under reduced pressure. Further preferred embodiments are described in the subclaims.

DETAILED DISCLOSURE

The methylglyoxal used in the present invention is as a rule industrial methylglyoxal which contains about 60% by weight of water. This aqueous methylglyoxal solution is preferably concentrated with respect to methylglyoxal to water contents of less than 40, particularly preferably less than 20, % by weight by distilling off water at 20–1013, particularly preferably 50–150, mbar, and, where the water contents are reduced to less than 5%, sparingly volatile solvents, for example relatively high-boiling alcohols (eg. decanol or diethylene glycol) or relatively high-boiling ethers (eg. diethylene glycol butyl ether) or similarly high-boiling solvents may be added to improve the stirability.

The actual reaction of methylglyoxal with methanol preferably takes place at a molar methylglyoxal: methanol ratio of from 1:2 to 1:50, preferably from 1:8 to 1:15.

The catalysis of the reaction is carried out, for example, in a conventional manner, for example at strongly acidic pH. Acidic ion exchangers in the form of fixed beds or as a suspension, as S commercially obtainable (for example BayKat 2611, Amberlyst 15, etc.), are preferably used as such acidic catalysts. The temperatures during the reaction over the catalysts are preferably from 20 to 120° C., particularly preferably from 50 to 90° C. The reaction need not necessarily lead to 100% conversion, and accordingly the duration of the reaction over the ion exchangers may vary.

A preferred reaction time is from 4 to 7, in particular from 5 to 6, hours and preferred reaction temperatures are from 50 to 100° C., in particular from 60 to 80° C.

In order to obtain the product, water is added to the reacted mixture; fractional distillation is then carried out, methylglyoxal dimethyl acetal surprisingly not being hydrolyzed by the added water although the pH of the reactor discharge is acidic (pH for example 2.0); furthermore, 1,1,2,2-tetramethoxypropane which is also formed and is an undesirable by-product is hydrolyzed to the desired product methylglyoxal dimethyl acetal. In the fractional distillation of the reaction product, after the low boilers and the excess methanol have been separated off, a single-phase mixture of MGDA-H$_2$O-methanol is advantageously initially taken up until methanol has been very substantially separated off from the reacted mixture. The azeotropic mixture of methylglyoxal dimethyl acetal and water (which may still contain a little methanol) which then passes over separates at the top into two phases, with the result that crude methylglyoxal dimethyl acetal can be obtained in a simple manner.

As stated above, the reaction can be carried out continuously or, preferably, batchwise. During the procedure, all substances involved in the process which still contain methylglyoxal dimethyl acetal, methylglyoxal or products convertible into methylglyoxal are continuously recycled to the process until, after a plurality of process steps, for example 12 process steps, a yield of, typically, over 80% of crude methylglyoxal dimethyl acetal is finally reached.

BRIEF DESCRIPTION OF THE PREFERRED EMBODIMENTS

Figure 1:
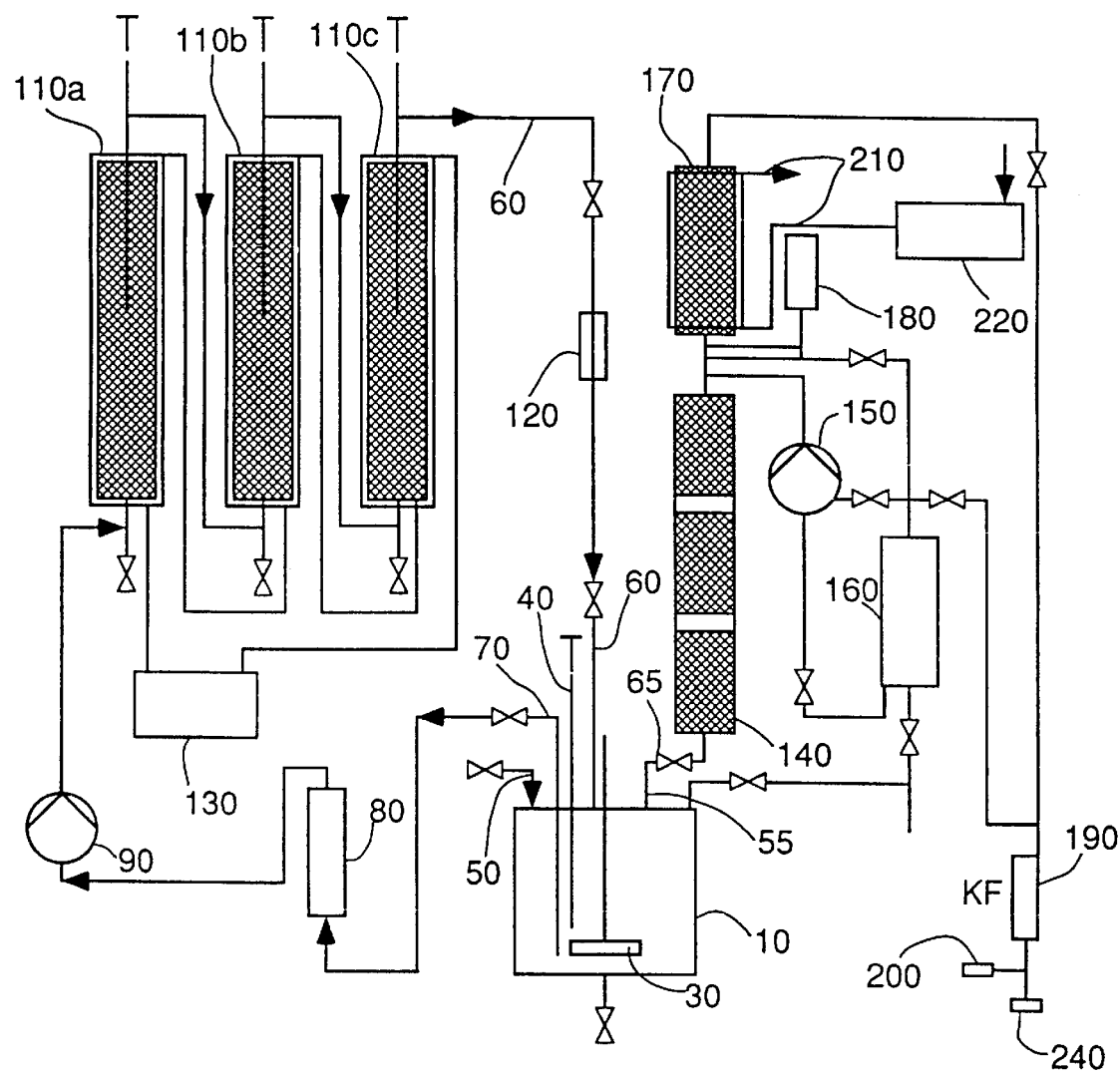
FIG. 1 is a partly schematic illustration of apparatus used in the process of the invention.

FIG. 1 shows a suitable apparatus for carrying out the process according to the invention by a batchwise method. A stirred kettle 10 is provided with a stirrer 30, a temperature sensor 40, a withdrawal line 70, a filling apparatus 50 and a feed line 60. The withdrawal line 70 leads via a flow meter 80 and a pump 90 to the reactors 110a, 110b and 110c, which are fixed-bed acidic ion exchangers which are kept at a desired temperature by means of the thermostat 130. After the desired reaction time, the discharge present in the stirred kettle is distilled via the column 140. The distillation apparatus is of conventional type with a reflux condenser 170, a water cooling means 210 whose temperature is regulated by means of the thermostat 220, a pump 150, a receiver 160, a reflux divider 180, a cold trap 190, a pressure controller 200 and a vacuum pump 240. A recycle line 55 provided with a valve 65 permits recycling of the bottom product of the column to the stirred kettle.

Figure 2:
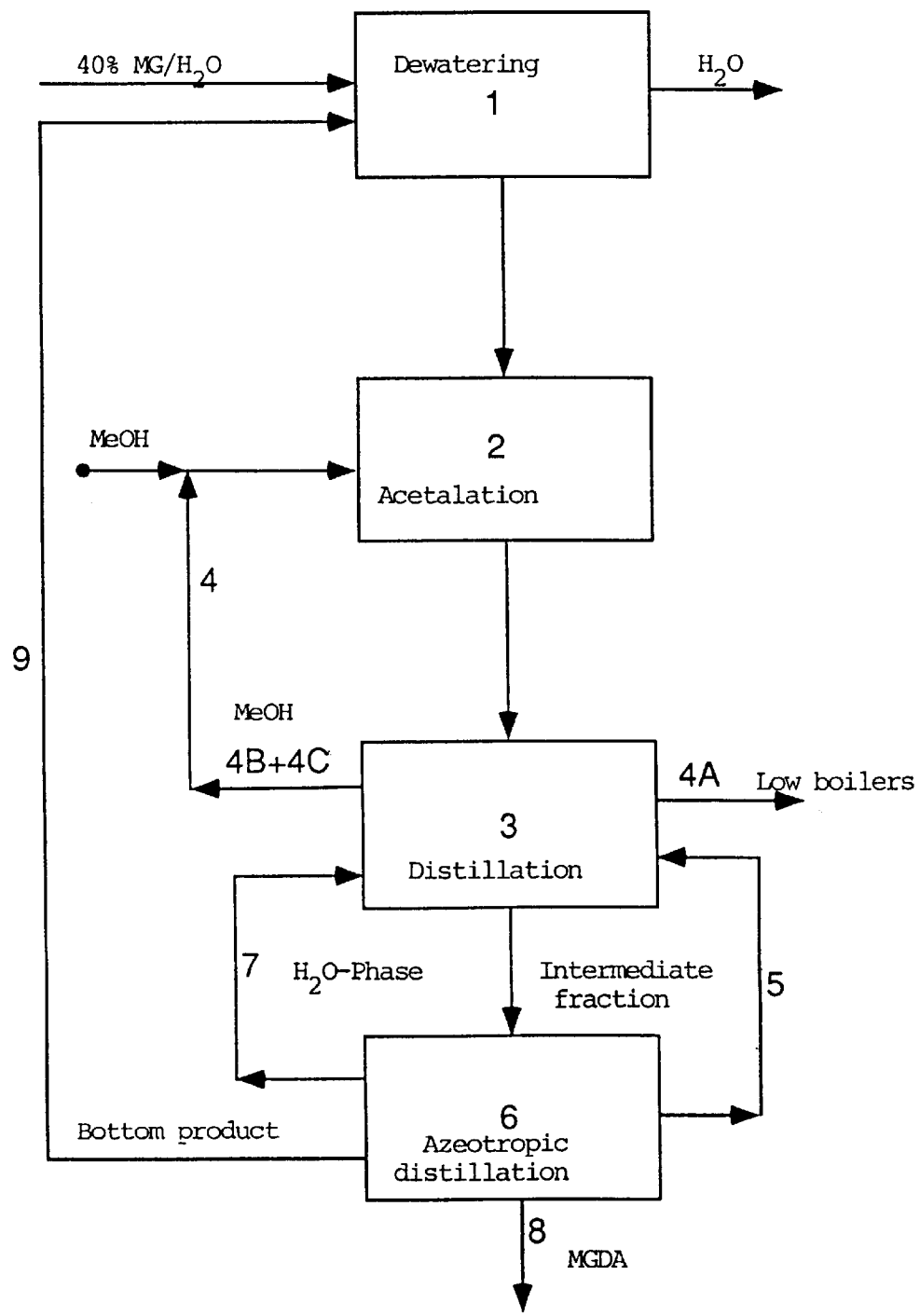
FIG. 2 is a schematic flow sheet or diagram based on FIG. 1.

FIG. 2 shows a basic flow diagram for a possible batchwise method for carrying out the novel process. In step 1, industrial methylglyoxal (MG) is concentrated by distilling off water. Before step 2, fresh methanol and, if required, recycled methanol are added, and the acetalation takes place in step 2. $H_2O$ is added to the reactor discharge, preferably after acetalation, and said discharge is then subjected to fractional distillation. In the distillation step 3, low-boiling fractions 4A are removed. Fractions 4B and 4C which contain mainly methanol, are distilled off and recycled to the next batch. An intermediate fraction 5 consisting of a single-phase mixture of methanol, MGDA and $H_2O$ is distilled off. This fraction is recycled to the next reaction step after the acetalation. The methylglyoxal is then separated off in stage 6 by azeotropic distillation, the azeotropic mixture separating at the top of the distillation column into two phases, ie. an aqueous phase 7, which is recycled to the bottom of the distillation 3 during the distillation, and a crude methylglyoxal dimethyl acetal phase, which is taken off as product 8 (MGDA). After the end of such a process step in the batchwise procedure, the bottom product 9 of the distillation is, if required, recycled to the starting material of the next step, which starting material may have to be dewatered (step 1).

Conditions for carrying out the process are, for example, a pressure of about 100 mbar, at which the water present is for the most part distilled off, for example, from an aqueous industrial methylglyoxal solution (about 60% by weight of water). After the addition of methanol, the mixture is then pumped, preferably at 65–75° C., for example for from 5 to 7 hours, over commercial acidic ion exchangers (eg. BayKat 2611, Amberlyst 15). At temperatures above the boiling point of methanol, the procedure is carried out under the autogenous pressure of the system. First, methanol and other low-boiling fractions are separated off until phase separation occurs in the top product of the column so that the methylglyoxal dimethyl acetal can be removed as a hetero azeotropic mixture. The remaining bottom product contains virtually no methylglyoxal dimethyl acetal (less than 0.3% by weight); it is recycled to the next process step. Surprisingly, the yield of methylglyoxal dimethyl acetal can thus be increased since the substances contained in the bottom product also form methylglyoxal dimethyl acetal with methanol, as has been shown in process stages in which no fresh methylglyoxal was added.

The Examples which follow illustrate the invention.

EXAMPLE 1A 438 g of diethylene glycol (4.125 mol) are initially taken in a 6 l stirred kettle and 986.5 g of 40.1% strength methylglyoxal (5.5 mol) are added.

At 100 mbar, the aqueous phase is distilled off until a bottom temperature of 80° C. is reached. The water content of the bottom product is then from 3 to 5% by weight. After cooling, 1760 g (55 mol) of methanol are added and the reaction mixture is then pumped for 5 hours at 70° C., under the autogenous pressure of the system, via the ion exchanger bed in the three reactors 110a, 110b, 110c. The autogenous pressure prevailing in the entire apparatus (the valve of the column is closed) is about 0.8 bar.

After the valves to the reactor have been closed, 500 ml of water are added to the reacted mixture in the stirred kettle, after is which distillation is carried out. The low-boiling fraction 4A of FIG. 2 is distilled off until a top temperature of 60° C. is reached.

Methanol (fraction 4B) is then distilled off with a variable reflux until the bottom temperature reaches 85° C., the top temperature being kept at 65° C. A variable reflux ratio up to 5:1 is maintained.

Reduced pressure of 500 mbar is then applied and further methanol is distilled off at a variable reflux ratio up to 10:1 (fraction 4C; boiling limit at the top=49° C.). The fractions 4B and 4C are combined and are recycled as recycled methanol (4=(4B+4C)) to the next batch before the reaction over the catalyst. Thereafter, the top temperature is limited to 74.5° C. and the intermediate fraction 5, which consists of a single-phase methylglyoxal dimethyl acetal/water/methanol mixture, is removed at 500 mbar. When 74.5° C. is reached, at which temperature methanol has been substantially removed, the azeotropic mixture passing over, which now comprises substantially methylglyoxal dimethyl acetal/water, undergoes phase separation. The methylglyoxal dimethyl acetal phase (8) is completely removed and the aqueous lower phase (7) is recycled until the methylglyoxal dimethyl acetal phase (8) no longer increases. 500 ml of the aqueous phase are then distilled off (7) from the stirred kettle with lowering of the reduced pressure to 100 mbar, said aqueous phase being recycled to the bottom in the next process step before the product is distilled off.

The intermediate fraction (5) and the bottom product (9) are also recycled to the process, as described in detail in Example 1B.

EXAMPLE 1B

This Example describes the procedure for one of the batchwise process stages which is not the first process stage. The bottom product (9) of the preceding batch is initially taken and 5.5 is mol of methylglyoxal are added. Water is then distilled off as in Example 1A and, after cooling, recovered methanol 4 is added and is supplemented, according to GC analysis, with fresh methanol so that a total of 1760 g (=55 mol) of methanol are present. The mixture is then reacted over the ion exchanger as in Example 1A. Thereafter, the intermediate fractions (5) and the aqueous phase (7) of the preceding batch are added to the stirred kettle and distillation is carried out as in Example 1A.

EXAMPLE 1C

Two batches are carried out in which only the bottom product (9) of the distillation of the last stage is further processed and no fresh methylglyoxal is added, the procedure otherwise being as in Example 1B.

After carrying out one process step as described in Example 1A, the further nine process steps as described in Example 1B and two process steps as described in Example 1C, a total of 4474.7 g of 86.5% strength crude methylglyoxal dimethyl acetal are obtained, corresponding to a total crude methylglyoxal dimethyl acetal yield of 84.4%. Table 1 below shows the compositions of the batch and of s the products. The MGDA 2 or MGDA $\Sigma_2$ phase (methylglyoxal dimethyl acetal which has been removed) comprises 86.5% of methylglyoxal dimethyl acetal, 9.1% of water and 1.6% of methanol (or is 86.5% strength).

TABLE 1

| Recycle | 0 (g/%) | 1st (g/%) | 2nd (g/%) | 3rd (g/%) |
|---|---|---|---|---|
| MG $\Sigma_{In}$ | 5.5 mol | 11.0 mol | 16.5 mol | 22.0 ml |
| MGDA 1 | 296.2/45.6 | 450.6/69.4 | 482.9/74.4 | 543.7/83.8 |
| MGTA 1 | 38.0/4.2 | 353/3.9 | 33.7/3.7 | 28.3/3.1 |
| MGTA $\Sigma_1$ | 38.0/4.2 | 73.3/4.1 | 107.0/4.0 | 135.3/3.8 |
| MGDA$\Sigma_1$ | 296.2/45.6 | 746.8/57.5 | 1229.7/63.1 | 1773.4/68.3 |
| MGDA 2 | 92.1/14.2 | 479.6/73.9 | 514.8/79.3 | 492.6/75.9 |
| MGDA$\Sigma_2$ | 92.1/14.2 | 571.7/44.0 | 1086.5/55.8 | 1579.1/60.8 |

TABLE 1-continued

| Recycle | 4th (g/%) | 5th* (g/%) | 6th (g/%) | 7th (g/%) |
|---|---|---|---|---|
| MG $\Sigma_{In}$ | 27.5 mol | 27.5 mol | 33.0 mol | 38.5 mol |
| MGDA 1 | 522.7/80.5 | 317A/48.9* | 424.0/65.3 | 500.7/77.1 |
| MGTA 1 | 31.9/3.5 | 32.5/3.6* | 51.3/5.7 | 33.0/3.7 |
| MGTA $\Sigma_1$ | 167.2/3.7 | 195.2/4.3 | 246.5/4.6 | 279.5/4.4 |
| MGDA$\Sigma_1$ | 2296.1/70.8 | 2613.5/80.5 | 3037.5/78.0 | 3538.2/77.9 |
| MGDA 2 | 563.4/86.8 | 266.1/41.0* | 581.1/89.5 | 394.7/60.8 |
| MGDA$\Sigma_2$ | 2142.5/66.0 | 2408.6/74.2 | 2989.7/76.8 | 3384.4/74.5 |

| Recycle | 8th (g/%) | 9th (g/%) | 10th (g/%) | 11th (g/%) |
|---|---|---|---|---|
| MG $\Sigma_{In}$ | 44.0 mol | 49.5 mol | 55.0 mol | 55.0 mol |
| MGDA 1 | 493.0/76.0 | 525.7/81.0 | 555.1/85.5 | 279.5/43.1 |
| MGTA 1 | 52.3/5.8 | 42.2/4.7 | 43.1/4.8 | 71.7/8.0* |
| MGTA $\Sigma_1$ | 331.8/4.6 | 374.0/4.6 | 417.1/4.6 | 488.8/5.4 |
| MGDA$\Sigma_1$ | 4031.2/77.6 | 4556.9/78.0 | 5112.0/78.8 | 5391.5/83.1 |
| MGDA 2 | 629.3/97.0 | 513.9/79.2 | 582.7/89.9 | 364.4/56.2 |
| MGDA$\Sigma_2$ | 4013.7/77.3 | 4527.6/77.5 | 5110.3/78.7 | 5474.7/84.4 |

MGDA 1: Yield of individual batch after circulation over BayKat 2611, based in each case on 5.5 mol MG
MGTA 1: 1,1,2,2-Tetramethoxypropane yield of the individual batch
MGDA $\Sigma_1$: Cumulative MGDA yield of the individual batches
MGTA $\Sigma_1$: Cumulative MGTA yield of the individual batches
MGDA 2: Yield of discharged MGDA of the individual batch
MGDA $\Sigma_2$: Cumulative yield of discharged MGDA
*Batch without addition of MG, the yield has been calculated hypothetically as 5.5 mol of MG

EXAMPLE 2

In Example 2, the experimental conditions are varied. No high-boiling solvent, such as diethylene glycol, is added to the reaction batch. The bottom temperature during the dewatering, which is s carried out at 100 mbar as in Example 1, is adjusted to 70° C. The H$_2$O content of the bottom product is about 10%. After a total of twelve such process steps, the total yield of discharged crude methylglyoxal dimethyl acetal is about 80%. Table 2 below gives the data of Example 2 in detail.

and 12.5 g of strongly acidic ion exchanger Dowex 50WX8 from Dow Chemical are refluxed for 16 hours. After the catalyst has been filtered off, analysis of the filtrate (percent by weight determined by gas chromatography, internal standard: dioxan) indicates that only 16.1 g (0.14 mol, 56%, based on methylglyoxal) of methylglyoxal dimethyl acetal have formed.

We claim:

1. In a process for the preparation and recovery of methylglyoxal dimethyl acetal by reacting a mixture of methylglyoxal and methanol in a reactor in the presence of an acidic catalyst to form the desired acetal product, the improvement which comprises:

carrying out the reaction at a molar methylgloxal:methanol ratio of from 1:2 to 1:50 and adding water to the reacted mixture;

initially distilling off excess methanol and low boiling impurities to obtain a single-phase azeotropic mixture consisting essentially of water and the acetal product;

subjecting said single-phase water and acetal mixture to an azeotropic distillation at reduced pressure and a temperature below 100° C. to remove both water and the acetal as a top product; and then condensing said top product and allowing it to stand and separate into a lower aqueous phase consisting essentially of water and an upper phase consisting essentially of said acetal product.

2. A process as claimed in claim 1, wherein said molar methylgloxal:methanol ratio is from 1:8 to 1:15.

3. A process as claimed in claim 1, wherein said acidic catalyst is a fixed bed of an acidic ion exchanger.

4. A process as claimed in claim 1, wherein said acidic catalyst is a suspension of an acidic ion exchanger.

5. A process as claimed in claim 1, wherein the process is carried out batchwise in two or more stages in which lower boiling components including methanol are recycled from one stage to the next, and the aqueous phase recovered from the azeotropic distillation is also recycled to the bottom in-

TABLE 2

| Process steps of Example 2 | 0 | 1 | 2 | 3 | 4 | 5 | 6 | 7 | 8 | 9 | 10 | 11 |
|---|---|---|---|---|---|---|---|---|---|---|---|---|
| MG In (cumulative, mol) | 5.5 | 11.0 | 16.5 | 22.0 | 27.5 | 27.5 | 33.0 | 38.5 | 44.0 | 49.5 | 55.0 | 55.0 |
| MGDA 4 (individual batch, g) | 306.0 | 399.9 | 472.3 | 464.9 | 509.9 | 288.5 | 405.8 | 459.5 | 467.1 | 520.0 | 513.1 | 331.5 |
| MGDA 4 (individual batch, mol %) | 47.1 | 61.6 | 72.8 | 71.6 | 78.6 | 44.5 | 62.5 | 70.8 | 72.0 | 80.1 | 79.1 | 51.1 |
| MGTA 4 (individual batch, g) | 44.6 | 47.2 | 31.2 | 38.7 | 27.6 | 19.8 | 28.8 | 27.6 | 54.2 | 28.6 | 32.9 | 33.6 |
| MGTA 4 (individual batch, mol %) | 4.9 | 5.2 | 3.5 | 4.3 | 3.1 | 2.2 | 3.2 | 3.1 | 6.0 | 3.2 | 3.6 | 3.7 |
| MGTA 4 (cumulative, g) | 44.6 | 91.8 | 123.0 | 161.7 | 189.3 | 209.1 | 237.9 | 265.5 | 319.7 | 348.3 | 381.2 | 414.8 |
| MGTA 4 (cumulative, mol %) | 4.9 | 5.1 | 4.5 | 4.5 | 4.2 | 4.6 | 4.4 | 4.2 | 4.4 | 4.3 | 4.2 | 4.6 |
| MGDA 4 (cumulative, g) | 306.0 | 705.9 | 1178.2 | 1643.1 | 2153.0 | 2441.5 | 2841.3 | 3306.8 | 3773.9 | 4293.9 | 4807.0 | 5138.5 |
| MGDA 4 (cumulative, mol %) | 47.1 | 54.4 | 60.5 | 63.3 | 66.3 | 75.2 | 73.1 | 72.8 | 72.7 | 73.5 | 74.1 | 79.2 |
| MGDA 7 (individual batch, g) | 217.4 | 393.6 | 421.2 | 531.3 | 497.8 | 341.9 | 394.1 | 450.8 | 465.3 | 514.0 | 521.5 | 416.4 |
| MGDA 7 (individual batch, mol %) | 33.5 | 60.6 | 64.9 | 81.9 | 76.7 | 52.7 | 60.7 | 69.5 | 71.7 | 79.2 | 80.4 | 64.2 |
| MGDA 7 (cumulative, g) | 217.4 | 611.0 | 1032.2 | 1563.5 | 2061.3 | 2403.2 | 2797.3 | 3248.1 | 3713.4 | 4227.4 | 4748.9 | 5165.3 |
| MGDA 7 (cumulative, mol %) | 33.5 | 47.1 | 53.0 | 60.2 | 63.5 | 74.1 | 71.8 | 71.5 | 71.5 | 72A | 73.2 | 79.6 |
| | | | | | | Recycling without addition of MG | | | | | | Recycling without addition of MG |

COMPARATIVE EXAMPLE 45 g of aqueous 40% strength methylglyoxal solution (0.25 mol of methylglyoxal), 185 g of methanol (5.78 mol)

the next batch process stage until the methylglyoxal dimethyl acetal phase no longer increases.

* * * * *